United States Patent
Sugita et al.

(10) Patent No.: US 6,723,732 B1
(45) Date of Patent: Apr. 20, 2004

(54) PERCUTANEOUSLY ADMINSTRABLE PREPARATIONS CONTAINING CEREBRAL FUNCTION ACTIVATORS

(75) Inventors: Katsuji Sugita, Osaka (JP); Yoshitaka Nishihara, Osaka (JP); Takayoshi Yoshikawa, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/830,113

(22) PCT Filed: Nov. 12, 1999

(86) PCT No.: PCT/JP99/06318

§ 371 (c)(1),
(2), (4) Date: Jul. 19, 2001

(87) PCT Pub. No.: WO00/29021

PCT Pub. Date: May 25, 2000

(30) Foreign Application Priority Data

Nov. 17, 1998 (JP) ............................. 10-326910
Jun. 14, 1999 (JP) ............................. 11-166759

(51) Int. Cl.⁷ ............................................... A61K 31/44
(52) U.S. Cl. ................................................... 514/293
(58) Field of Search ........................................ 514/293

(56) References Cited

U.S. PATENT DOCUMENTS 5,378,848 A   1/1995   Takada et al. ............... 546/82

FOREIGN PATENT DOCUMENTS

| EP | 480054 | 4/1992 |
| EP | 556008 | 8/1993 |
| EP | 581587 | 2/1994 |
| EP | 682942 | 11/1995 |
| JP | 5-25046 | 2/1993 |

OTHER PUBLICATIONS

Miyamoto et al., European Journal of Pharmacology, 271, pp. 357–366 (1994).

Sugibayashi et al., Fragrance Journal 1996–4, pp. 17–25.

Morimoto et al., International Journal of Pharmaceutics, 91, pp. 9–14 (1993).

Wada et al., Biol. Pharm. Bull. 16(6), pp. 600–603 (1993).

*Primary Examiner*—Phyllis Spivack
*Assistant Examiner*—C. Delacroix-Muirheid
(74) *Attorney, Agent, or Firm*—Wenderoth, Lind & Ponack, LLP

(57) ABSTRACT

The present invention provides a percutaneously administrable preparation comprising either an aqueous base comprising 1-menthol, a lower alcohol and an acidic buffer or water, or an oily base comprising 1-menthol, a lower alcohol and isopropyl myristate, and a cerebral function activator, for example, 2-(3-isoxazolyl)-3,6,7,9-tetrahydroimidazo[4,5-d]pyrano[4,3-b]pyridine, pharmaceutically acceptable salt or hydrate thereof.

2 Claims, 3 Drawing Sheets

*: P<0.05 (Dunnett's test)

PERCUTANEOUSLY ADMINSTRABLE PREPARATIONS CONTAINING CEREBRAL FUNCTION ACTIVATORS

This application is a 371 of PCT/JP99/06318 filed Nov. 12, 1999.

TECHNICAL FIELD

The present invention relates to a percutaneously administrable preparation containing a cerebral function activator, specifically, a percutaneously administrable preparation containing an imidazopyridine derivative as a cerebral function activator.

BACKGROUND ART

A compound of the formula (I):

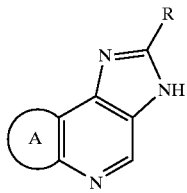

wherein R is optionally substituted aryl or optionally substituted heteroaryl, A ring is a 5- to 9-membered alicyclic group which may contain one or more of O, S, SO, $SO_2$ and/or $NR^1$ wherein $R^1$ is hydrogen, alkyl, esterified carboxy, carbamoyl or acyl, and which may be substituted with alkyl, pharmaceutically acceptable salt or hydrate thereof (hereinafter referred to as Compound (I)) is described in JP 5-286973 A and known to be useful as a psychotropic agent, an antianxiety agent, a narcotic antagonist and a cerebral function activator.

It has been reported that a pharmaceutical activity of a cerebral function activator was enhanced by being administered in a sustained release depot form (European Journal of Pharmacology, 271, 357–366, 1994), but it is not known that the effect of the cerebral function activator can be prolonged by being administered in a percutaneously administrable preparation.

The drug absorption rate from skin is generally slower than that at mucous membrane such as gastrointestinal tract etc., and a large number of studies have been conducted on absorption enhancing agents in order to increase the percutaneous absorption. Absorption enhancing agents, such as DMSO, various surface active agents, 1-dodecylazacycloheptan-2-one, fatty acids, terpenes, alcohols, and mixtures (e.g., 1-menthol-ethanol-water, lactic acid-ethanol-isopropyl myristate and the like), have been studied (Fragrance Journal 1996(4), 17–25). In these studies, however, a preparation containing a cerebral function activator or a condensed imidazopyridine derivative as an active ingredient has not been investigated.

DISCLOSURE OF INVENTION

An object of the present invention is to provide a percutaneously administrable preparation which contains a cerebral function activator, specifically, a condensed imidazopyridine derivative as an active ingredient and which can sustain an effective blood concentration and the efficacy of the active ingredient by suppressing an extreme raise of the blood concentration after the administration.

The present invention relates to 1) a percutaneously administrable preparation, which comprises either an aqueous base comprising 1-menthol, a lower alcohol and an acidic buffer or water, or an oily base comprising 1-menthol, a lower alcohol and isopropyl myristate, and a cerebral function activator therein, 2) the percutaneously administrable preparation described in 1) wherein the cerebral function activator is a compound of the formula (I):

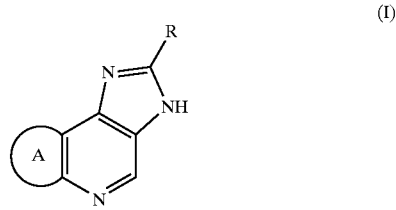

wherein R is optionally substituted aryl or optionally substituted heteroaryl and A ring is a 5- to 9-membered alicyclic group which may contain one or more of O, S, SO, $SO_2$ and/or $NR^1$ wherein $R^1$ is hydrogen, alkyl, esterified carboxy, carbamoyl or acyl, and which may be substituted with alkyl, pharmaceutically acceptable salt or hydrate thereof, 3) the percutaneously administrable preparation described in 1) or 2) wherein the cerebral function activator is 2-(3-isoxazolyl)-3,6,7,9-tetrahydroimidazo[4,5-d]pyrano[4,3-b]pyridine, pharmaceutically acceptable salt or hydrate thereof, 4) the percutaneously administrable preparation described in 3) wherein the cerebral function activator is 2-(3-isoxazolyl)-3,6,7,9-tetrahydroimidazo[4,5-d]pyrano[4,3-b]pyridine phosphate or hydrate thereof, 5) the percutaneously administrable preparation described in 1) to 4) wherein the percentage of 1-menthol to all amount of the base is 1 to 3.5% by weight, 6) the percutaneously administrable preparation described in 1) to 5) wherein the percentage of the lower alcohol to all amount of the base is 10 to 35% by weight, 7) the percutaneously administrable preparation described in 1) to 6) wherein the lower alcohol is a lower alcohol having 1 to 3 carbon atoms, 8) the percutaneously administrable preparation described in 1) to 7) wherein the lower alcohol is ethanol, 9) the percutaneously administrable preparation described in 1) to 8) wherein the percentage of the acidic buffer, water or isopropyl myristate to all amount of the base is 55 to 90% by weight, 10) the percutaneously administrable preparation described in 1) to 9) wherein pH of the acidic buffer is 2 to 6, 11) the percutaneously administrable preparation described in 1) to 10) wherein the acidic buffer is a phosphate buffer, 12) the percutaneously administrable preparation described in 1) to 4), wherein each percentage to all amount of the base: 1-menthol is 2 to 3% by weight, ethanol is 15 to 35% by weight, the phosphate buffer, water or isopropyl myristate is 60 to 80% by weight, and pH of the acidic buffer is 3 to 5, and 13) the percutaneously administrable preparation described in 1) to 12) comprising 1 to 25 mg of the cerebral function activator per 1 g of the base.

An orally administrable preparation generally tends to lack the sustained efficacy due to the extreme raise of blood concentration. A preparation of the present invention overcomes such a problem and has the following advantages. The percutaneously administrable preparation of the present invention can reduce individual differences of the blood concentration by avoiding the hepatic first-pass effect. The preparation shows a continuously pharmacological efficacy because the plasma concentration of the active ingredient can be kept constant for a long duration by the sustained release to whole body blood circulation. Further, the preparation scarcely causes side effects, e.g., a gastrointestinal injury which often occurs upon oral administration.

BEST MODE FOR CARRYING OUT THE INVENTION

Figure 1:
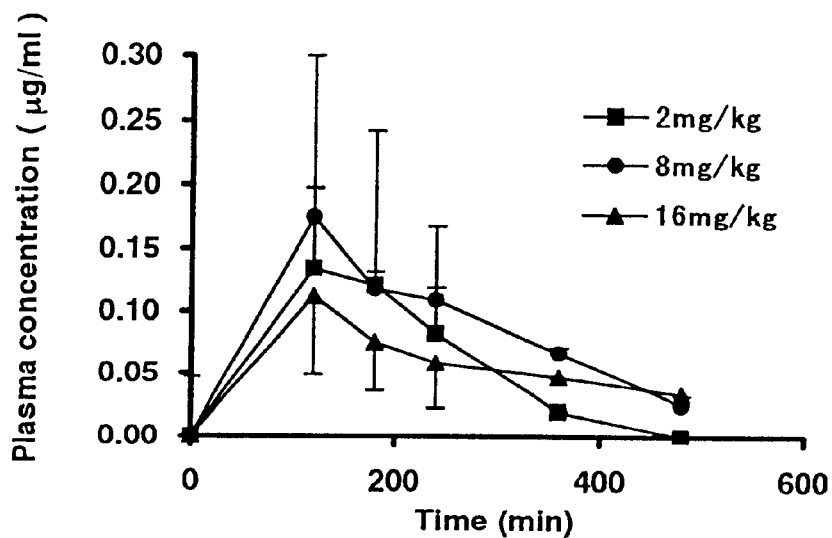
FIG. 1 shows a plasma concentration-time courses of the preparation of the present invention using a phosphate buffer at followings dose. ■ indicates 2 mg/kg dose, ● indicates 8 mg/kg dose and ▲ indicates 16 mg/kg dose.

In the present specification, the term "aryl" includes phenyl, naphthyl, anthryl, indenyl, phenanthryl and the like.

The term "optionally substituted aryl" includes the above mentioned "aryl" which may have one or more of substituents selected from alkyl, hydroxy, alkoxy, aryloxy, acyloxy, carboxy, ester (e.g., alkoxycarbonyl, aralkoxycarbonyl etc.), cyano, amino, mono- or di-substituted amino, hydrazino, hydroxyamino, alkoxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. Preferable examples are substituted or unsubstituted phenyl and the examples of substituents for phenyl are methyl, methoxy, chloro and the like.

The term "heteroaryl" means a cyclic group containing one or more of hetero atoms arbitrarily selected from O, S and N in the ring and the cyclic group may condense with a carbocycle or another heterocycle. The examples of "heteroaryl" are 5- to 6-membered heteroaryl such as pyrrolyl, imidazolyl, pyrazolyl, pyridyl, pyridazinyl, pyrimidinyl, pyrazinyl, triazinyl, isoxazolyl, oxazolyl, oxadiazolyl, isothiazolyl, thiazolyl, thiadiazolyl, furyl, thienyl etc., and condensed heteroaryl such as indolyl, benzimidazolyl, indazolyl, indolizinyl, quinolyl, isoquinolyl, cinnolinyl, phthalazinyl, quinazolinyl, naphtyridinyl, quinoxalinyl, pteridinyl, benzisoxazolyl, benzoxazolyl, oxadiazolyl, benzoxadiazolyl, benzisothiazolyl, benzothiazolyl, benzothiadiazolyl, benzofuryl, benzothienyl, carbazolyl, phenazinyl etc.

As the substituents for "optionally substituted heteroaryl", exemplified are alkyl, hydroxy, alkoxy, carboxy, ester (e.g., alkoxycarbonyl, aralkoxycarbonyl etc.), cyano, amino, mono- or di-substituted amino, hydrazino, hydroxyamino, alkoxyamino, halogen, nitro, acyl, carbamoyl, thiocarbamoyl, carbamoyloxy, thiocarbamoyloxy, ureido, thioureido, sulfonamide, mono- or di-substituted sulfonamide, sulfonic acid, halogenoalkyl, hydroxyalkyl, alkoxyalkyl, acyloxyalkyl, nitroalkyl, aminoalkyl, acylaminoalkyl, cyanoalkyl, carboxyalkyl and the like. These substituents may substitute at one or more of possible positions. The substituents are preferably unsubstituted 5-membered heteroaryl, more preferably unsubstiuted thienyl, unsubstituted furyl, unsubstituted isoxazolyl or unsubstituted pyridyl, and most preferably unsubstituted isoxazolyl.

"A 5- to 9-membered alicyclic group which may contain one or more of O, S, SO, $SO_2$ and/or $NR^1$ wherein $R^1$ is hydrogen, alkyl, esterified carboxy, carbamoyl or acyl, and which may be substituted with alkyl" condenses with the neighboring pyridine ring. The examples of alicyclic groups are a carbocyclic group such as a cyclopenteno ring, a cyclohexeno ring, a cyclohepteno ring, a cycloocteno ring, a cyclononeno ring etc., a heteroalicycle such as pyrrolidino, pyrrolino, imidazolidino, pyrazolidino, dihydrothiopheno, dihydrofurano, thiazolino, dihydropyranno, dihydrothiopyrano, piperidino, piperazino, morpholino, thiomorpholino, tetrahydropyridino, and tetrahydropyrimidino etc. Dihydropyrano, dihydrothiopyrano or piperidinno is preferable and dihydropyrano is especially preferable. These rings may be substituted with alkyl (e.g., one or two methyl, ethyl or the like).

The term "alkyl" includes a straight or branched alkyl having 1 to 10 carbon atoms and a lower alkyl having 1 to 6 carbon atoms is preferable. For example, methyl, ethyl, n-propyl, isopropyl, n-butyl, sec-butyl, tert-butyl, n-pentyl, isopentyl, neopentyl, tert-pentyl, 2-methylbutyl, n-hexyl, isohexyl, heptyl, isoheptyl, octyl, isooctyl, nonyl, decyl and the like are included.

The alkyl parts of "halogenoalkyl", "hydroxyalkyl", "alkoxyalkyl", "acyloxyalkyl", "nitroalkyl", "aminoalkyl", "acylaminoalkyl", "cyanoalkyl" and "carboxyalkyl" are the same as the above "alkyl".

The term "esterified carboxy" includes methoxycarbonyl, etboxycarbonyl, tert-butoxycarbonyl, benzyloxycarbonyl and the like.

The term "acyl" includes an aliphatic acyl having 1 to 10 carbon atoms and an aromatic acyl. The examples are formyl, acetyl, propionyl, butyryl, isobutyryl, valeryl, pivaloyl, hexanoyl, acryloyl, propioloyl, methacryloyl, crotonoyl, cyclohexanecarbonyl, benzoyl, 4-nitrobenzoyl, 4-tert-butylbenzoyl, benzenesulfonyl, toluenesulfonyl and the like.

The term "alkoxy" includes straight or branched alkoxy having 1 to 10 carbon atoms and a lower alkoxy having 1 to 6 carbon atoms is preferable. The examples are methoxy, ethoxy, n-propoxy, isopropoxy, n-butoxy, isobutoxy, secbutoxy, tert-butoxy, n-pentyloxy, isopentyloxy, neopentyloxy, tert-pentyloxy, 2-methylbutoxy, n-hexyloxy, isohexyloxy, heptyloxy, isoheptyloxy, octyloxy, isooctyloxy, nonyloxy, decyloxy and the like.

The alkoxy parts of "alkoxycarbonyl", "alkoxyamino", "alkoxyalkyl" and "aralkoxycarbonyl" are the same as the above "alkoxy".

The acyl parts of "acyloxy", "acylaminoalkyl" and "acyloxyalkyl" are the same as the above "acyl".

The aryl parts of "aryloxy" and "aralkoxycarbonyl" are the same as the above "aryl".

The substituents for "mono- or di-substituted amino" and "mono- or di-substituted sulfonamide" include one or two of hydroxy, halogen, alkyl, alkenyl, acyl, aryl and the like.

The term "halogen" includes fluorine, chlorine, bromine and iodine.

In the specification, the term "cerebral function activator" includes a brain metabolic stimulant, an ameliorants of cerebral circulation and the like and means a drug for treating cerebrovascular disease, head injury, postoperative sequela, dementia and the like. For example, γ-amino-β-hydroxy butyric acid, meclofenoxate hydrochloride, calcium potenate, idevenone, indeloxazine hydrochloride, citicoline, amantadine hydrochloride, lisuride maleate, tiapride hydrochloride, bifemelane hydrochloride, ifenprodil tartrate, bencyclane fumarate, cinepazide maleate, pentoxyfylline, vinpocetine, dihydroergotoxine mesilate, nicardipine hydrochloride, cinnarizine, flunarizine, donepezil, Compound (I) and the like are included. Compound (I) is preferable.

Compound (I) includes three kinds of tautomers and the above mentioned formula (I) is just an example. Compound (I) includes other tautomers, i.e., Compound (I') having double bonds at the 2-3, 3a-3b and 4-5 position and Compound (I") having double bonds at the 1-3b, 2-3 and 3a-4 position of the following formulae.

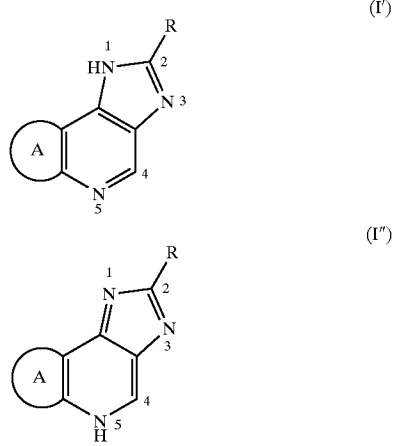

"Compound (I)" includes any possible pharmaceutically acceptable salt of each compound. As the "pharmaceutically acceptable salt", exemplified are salts with mineral acids such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid, methanesulfonic acid, benzenesulfonic acid, p-toluenesulfonic acid and the like; salts with acidic amino acids such as ornithine, aspartic acid, glutamic acid and the like. Phosphate is preferable.

"Compound (I)" includes hydrates thereof, wherein arbitrary numbers of water molecules may coordinate to the compound (I).

Any of the compound (I) can be used for the preparation of the present invention, and 2-(3-isoxazolyl)-3,6,7,9-tetrahydroimidazo[4,5-d]pyrano[4,3-b]pyridine (hereinafter referred to as Compound (I-1)), phosphate or hydrate thereof is especially preferable.

As 1-menthol, a lower alcohol (e.g., ethanol, isopropanol etc.) and isopropyl myristate for the preparation of the present invention, may be used those listed in The Japanese Pharmacopoea Twelfth Edition, The Pharmaceutical Additives Standard 1998, The Official Formulary of Food Additives Sixth Edition, The Cosmetic Material Standard Second Edition or the like.

The amount of 1-menthol in the base can be appropriately changed according to the kind, the concentration and the amount of the active ingredient. The percentage of 1-menthol is 1–3.5% by weight, preferably 2–3% by weight to all amount of the base. If the amount of 1-menthol is more than the above range, the preparation is not preferable for percutaneous administration because of the skin irritation. On the other hand, when the amount of 1-menthol is less than the above range, the preparation can not show a sufficient pharmacological effect because of the decrease of the absorption rate.

The examples of "lower alcohol" used in the present preparation are a lower alcohol having 1 to 3 carbon atoms and the like. Concretely, methanol, ethanol, propanol, isopropanol and the like are exemplified and ethanol is especially preferable.

The amount of a lower alcohol in the base can be appropriately changed depending on the kind, the concentration and the amount of the active ingredient, or the kind of the lower alcohol. The percentage of the lower alcohol is 10–35% by weight, preferably 15–35% by weight and more preferably 20–30% by weight to all amount of the base. If the amount of the lower alcohol is more than the above range, the preparation is not preferable for percutaneous administration because of the skin irritation. On the other hand, when the amount of the lower alcohol is less than the above range, the preparation can not show a sufficient pharmacological effect because of the decrease of the absorption rate. Furthermore, in the aqueous base, 1-menthol tends to precipitate when the amount of lower alcohol decreases because the compatibility of 1-menthol dissolved in the lower alcohol and an acidic buffer or water decreases.

As an acidic buffer used in the preparation of the present invention, any acidic buffer which can adjust the pH value to 1–6, preferably 3–5 may be used. Examples of the buffer are phosphate, tartrate, citrate, acetate etc. and a phosphate buffer is preferable. These buffers may be commercially available or appropriately prepared in the usual manner. For example, 1/15 mol of potassium dihydrogen phosphate is dissolved in 1 ml of water to prepare an aqueous solution of pH 9. The pH of the obtained solution can be suitably adjusted using phosphoric acid, disodium hydrogen phosphate or the like to obtain a buffer having the target pH.

A preferable range of pH value is 1–6, more preferably 3–5. If the value of pH is higher than the above range, the absorption rate of the preparation decreases. If the value of pH is lower than the above range, the preparation causes the skin irritation. Therefore, such preparations can not be preferably used.

Water can be used in place of the acidic buffer. For example, in the case that the cerebral function activator is an acidic compound, the preparation of the present invention can be used without adjusting the pH value because it is already acidic. In other cases, the value of pH may be appropriately adjusted using phosphoric acid or the like, if necessary.

The choice of ingredient of the base among a phosphate buffer, water and isopropyl myristate depends on the kind of the active ingredient and a target dosage form. The choice also depends on the kind of the base, i.e., an aqueous or an oily base. For the pharmaceutical manufacturing of an adhesive preparation, the oily base such as isopropyl myristate is preferable.

The amount of the phosphate buffer, water or isopropyl myristate can be appropriately changed depending on the kind, the concentration or the amount of the active ingredient, or the kind or pH of the buffer. For example, the percentage of the phosphate buffer or water is 55–90% by weight, preferably 60–80% by weight, and more preferably 60–70% by weight to all amount of the base. The percentage of isopropyl myristate is 55–90% by weight, preferably 65–85% by weight, and more preferably 70–80% to all amount of the base.

If the amount of the buffer, water or isopropyl myristate is more than the above range, the concentration of the active ingredient in a dosage form can be high because the dissolvable amount of the active ingredient increases. However, to obtain a high absorption rate, a certain amount of 1-menthol and a lower alcohol must be contained in the base. Therefore, the amount of the buffer, water or isopropyl myristate should be determined in consideration of the amount of 1-menthol and the lower alcohol.

On the other band, if the amount of the buffer, water or isopropyl myristate is less than the above range, the dose must be increased to obtain the sufficient absorption of the active ingredient because the dissolvable amount of the active ingredient decreases. As a result, the dose becomes inappropriately so high or the area to be applied becomes inappropriately so wide that the preparation can not be preferably applied. If such preparation is not applied at high-dose or to wide area, sufficient pharmaceutical effect can not be obtained.

In the preparation of the present invention, the active ingredient may be dissolved or dispersed 1–25 mg, preferably 5–10 per 1 g of the base. The addition of the active ingredient more than the above range is not preferable because the ingredient can not be uniformly dissolved or dispersed and absorbed into the body.

If the amount of the active ingredient is smaller than the above range, the dose must be increased for obtaining the objective absorption rate and, therefore, the application area must be inappropriately enlarged. As a result, the preparation can not be a preferable preparation. If the dose decreases, the preparation can not show the objective pharmaceutical effect and can not be a sustained release preparation which gives a sufficient effect by once a day application.

Examples of the percutaneously administrable preparation of the present invention include ointments, creams, solutions, gels, liniments, lotions, tapes, poultices, patches etc., which can be prepared by the generally known method.

For example, at first, 1-menthol, the lower alcohol and the phosphate buffer, water or isopropyl myristate are uniformly mixed in an appropriate mixing ratio.

An cerebral function activator, the active ingredient (for example, Compound (I)), is added to the mixture and the mixture was exposed to ultrasonic waves for about 10–15 minutes, followed by additional stirring, if necessary.

Then, the preparation is prepared in a suitable method according to the type of the form such as ointments, patches or the like. Additives which are generally used for percutaneously administrable preparations can be appropriately selected, added and mixed thereto. Examples of additives are a vehicle such as vaseline, PEG 400, PEG 4000 etc., an antiseptic such as methylparaben, ethylparaben etc., a stabilizer such as EDTA-2Na, calcium hydroxide etc., a pH regulator such as tartaric acid, citric acid etc., a surfactant such as sorbitan monooleate, polyoxyethylene sorbitan monooleate etc., a moisturizer such as glycerin, propylene glycol, 1,3-butylene glycol etc., an antioxidant such as ascorbic acid, vitamin E, butylhydroxytluene etc., a suspending agent such as arabian gum, sodium alginate etc., softener such as liquid paraffin etc., a tackifier such as gelatin, arabian gum, glycerin, acrylic polymer, rubber polymer, silicone polymer, $\alpha$-pinene etc., a coloring agent such as kaolin, titanium oxide etc., a flavor and the like.

For preparing patches, the mixture of the active ingredient and the base obtained by the above-mentioned method may be absorbed to or spread on an appropriate support (i.e., cloths, non-wave cloths, papers, rubber sheets, foam sheets, plastic films and the like). In a preferred embodiment, the mixture of the active ingredient and the base is mixed with a tackifier, then the obtained paste-like mixture is spread on the support. After uniformly spreading the mixture, the surface may be covered with a release paper such as a silicone-treated polyethylene terephthalate film, a polyethylene-coated glassine paper, a polyester film, a polypropylene film or the like until administration. Conversely, the mixture of the active ingredient and base may be spread on the release paper, followed by putting the support thereon.

The dosage of the preparation of the present invention should be determined in consideration of the kind and concentration of the active ingredient, patient's age, and the type and degree of diseases. For example, a preparation which can administer the active ingredient in an amount of 2.5–20 mg/day may be administered to an adult once a day. If necessary, the preparation may be administered in several divisions per a day.

The area for the application of the preparation of the present invention is not particularly limited and the preparation may be applied to any area where the active ingredient is suitably absorbed. For example, arms, feet, back of ear, nape of the neck, breast or the like is preferable.

The present invention is further explained by the following Examples and Experiments, which are not intended to limit the scope of the present invention.

EXAMPLES

Experiment 1

1) Experimental Method (I) A base was composed of 2.5% 1-menthol/20% ethanol/77.5% distilled water. The phosphate salt of Compound (I-1) as an active ingredient was dissolved or dispersed in it at concentrations of 1.4, 5.6, and 11.2 mg/mL.

(II) To Non-fasting rats (Jcl SD strain rat, 9–10 weeks old) was injected 20% urethane solution subcutaneously (0.65 mL/100 g BW). After the anesthetic condition of the rat became stable, abdominal hair was removed using a hair clipper and shaver, then the rats were kept on a hotplate at 36° C. A glass cell (35 mm I.D. with a ground stopper) was attached using Aron alpha (trademark) in an abdominal region of the rat and absorbent gauze (about two sheets) was placed in the cell, then 0.5 mL of the above obtained pharmaceutical preparations of the invention was administrated to the cell (2, 8 or 16 mg/kg, N=3).

(III) The time of blood collection: 0, 1, 2, 3, 4, 6, and 8 hr after the administration (IV) After the blood collection at 8 hrs, the residual drug in pharmaceutical preparations of the present invention in the cell was recovered by the addition of 50 mL of methanol. The percent of apparent absorption was calculated by the difference between the initial dose and the recovered amount at 8 hrs. AUC and MRT were calculated from plasma concentration profiles measured by HPLC. Furthermore, the skin to which the applied pharmaceutical preparations were applied and their subcutaneous part were removed and macroscopically checked after the experiments.

Results are represented in Table 1 and FIG. 1.

TABLE 1

| Dose (mg/kg) | AUC (μg * hr/ml) | MRT (hr) | Percent of apparent absorption (%) |
|---|---|---|---|
| 2 | 0.49 ± 0.50 | 3.4 ± 0.6 | 71.3 |
| 8 | 0.72 ± 0.05 | 3.6 ± 0.2 | 81.0 |
| 16 | 0.46 ± 0.18 | 4.0 ± 0.7 | 35.8 |

No irritations were observed in all doses.

The results from Table 1 and FIG. 1 show that the pharmaceutical preparations of the present invention produce prolonged plasma concentrations and are expected to show long time effect of the drug.

Experiment 2

Figure 2:
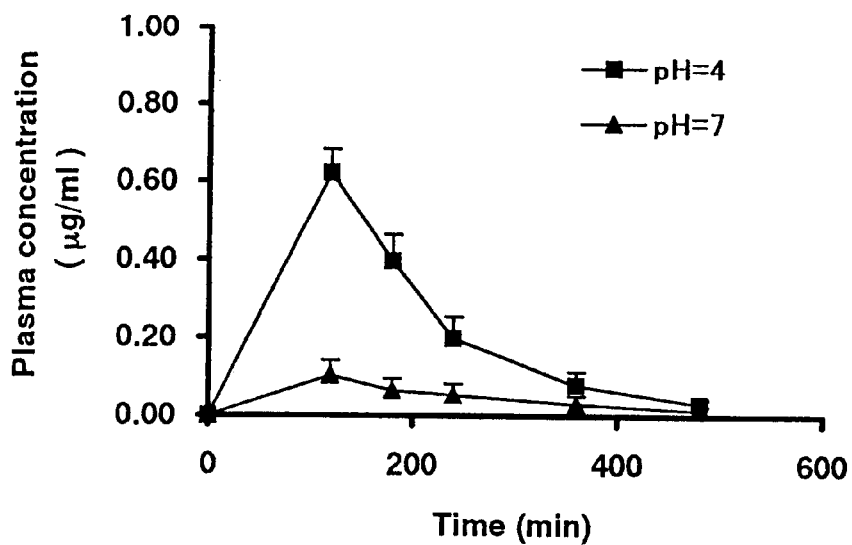
FIG. 2 shows a plasma concentration-time courses of the preparation of the present invention at pH 4 and 7. ■ indicates a preparation using a base of pH 4 and ▲ indicates a preparation using a base of pH 7.

A phosphate buffer of pH 9 was prepared from $\frac{1}{15}$ mole of dibasic sodium phosphate dissolved in 1 mL of distilled water. The phosphate buffers of pH 4 and pH 7 were prepared by the addition of phosphoric acid to the pH 9 buffer. A bBase was composed of 3% 1-menthol/30% ethanol/67% phosphate buffer. The phosphate salt of Compound (I-1) as an active ingredient was dissolved or dispersed in the base at a concentration of 5.6 mg/mL. Other conditions were the same as that of Experiment 1 (N=3). Results are represented in Table 2 and FIG. 2.

TABLE 2

| pH | AUC (μg * hr/ml) | MRT (hr) | Percent of apparent absorption (%) |
|---|---|---|---|
| 4 | 1.81 ± 0.30 | 3.0 ± 0.2 | 66.8 |
| 7 | 0.38 ± 0.18 | 3.4 ± 0.3 | 22.6 |

No irritations were observed in all formulations.

Experiment 3

Bases studied in Experiment 3 were listed in Table 3. The phosphate salt of Compound (I-1) as an active ingredient was dissolved or dispersed in bases in Table 3 at a concentration of 5.6 mg/mL. Other condition were the same as that of the Experiment 1. The percent of apparent absorption was calculated and listed in Table 3.

TABLE 3

| | Base | Percent of apparent absorption (%) |
|---|---|---|
| | 2.5% l-menthol, 20% ethanol, 77.5% isopropyl myristate | 28.1 |
| Reference examples | 5% ethanol, 95% isopropyl myristate | 13.0 |
| | 5% lactic acid, 5% ethanol, 90% isopropyl myristate | 11.9 |
| | 5% N-methyl pyrrolidone, 5% ethanol, 90% isopropyl myristate | 17.4 |

In reference examples, the concentrations of Compound (I-1) in all plasma samples were under the limit of detection (50 ng/mL).

Experiment 4

Figure 3:
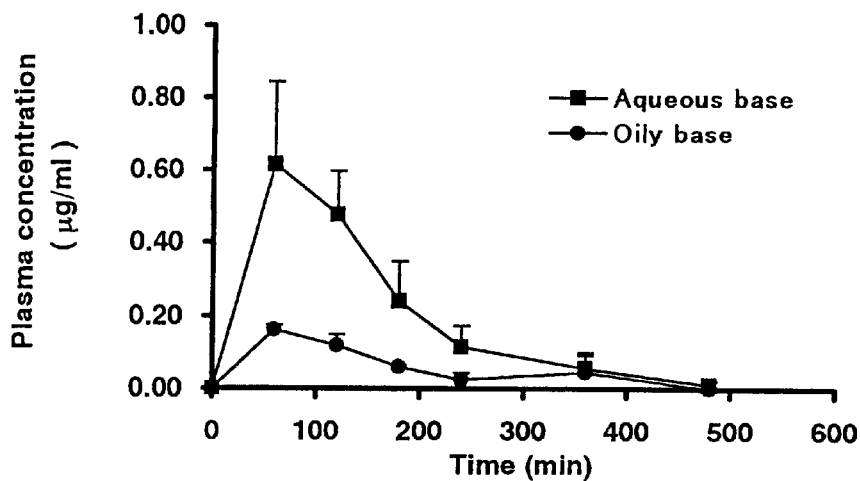
FIG. 3 shows a plasma concentration-time courses of the preparation of the present invention using an aqueous or oily base. ■ indicates a preparation using an aqueous base and ● indicates a preparation using an oily base.

The 3% 1-menthol/30% ethanol/67% pH 4 phosphate buffer was selected as an aqueous base. The 2.5% 1-menthol/20% ethanol/77.5% isopropyl myristate was selected as an oily base. The phosphate salt of Compound (I-1) as an active ingredient was dissolved or dispersed in the aqueous or oily formulation at a concentration of 5.6 mg/mL. Other conditions were the same as that of Experiment 1 (N=3). Cmax, Tmax, MRT and AUC were calculated and listed in Table 4 and FIG. 3.

TABLE 4

| | Cmax (μg/ml) | Tmax (hr) | MRT (hr) | AUC (μg * hr/ml) |
|---|---|---|---|---|
| Aqueous base | 0.69 ± 0.13 | 1.3 ± 0.6 | 2.2 ± 0.5 | 1.61 ± 0.30 |
| Oily base | 0.16 ± 0.01 | 1.0 ± 0.0 | 2.6 ± 0.6 | 0.47 ± 0.10 |

Experiment 5

The experiment was performed by the strapping technique under the conscious condition. Non-fasting rats (Jcl Wistar strain male rat 9–11 W) were cannulated in the jugular vein two days before the percutaneous administration experiment. On the day of experiment, abdominal region hair of rats were removed using a hair clipper and shaver under ether anesthesia. Three different volumes (0.125, 0.25, and 0.5 mL) of the aqueous basic formulation (3% 1-menthol/30% ethanol/67% pH 4 phosphate buffer) containing 5.6 mg/mL of Compound (I-1) were administered (2, 4, and 8 mg/kg) on the rayon cloths, which area were 2.5, 5, and 10 cm², respectively, supported by tape on the abdominal region then covered with gum tape.

Figure 4:
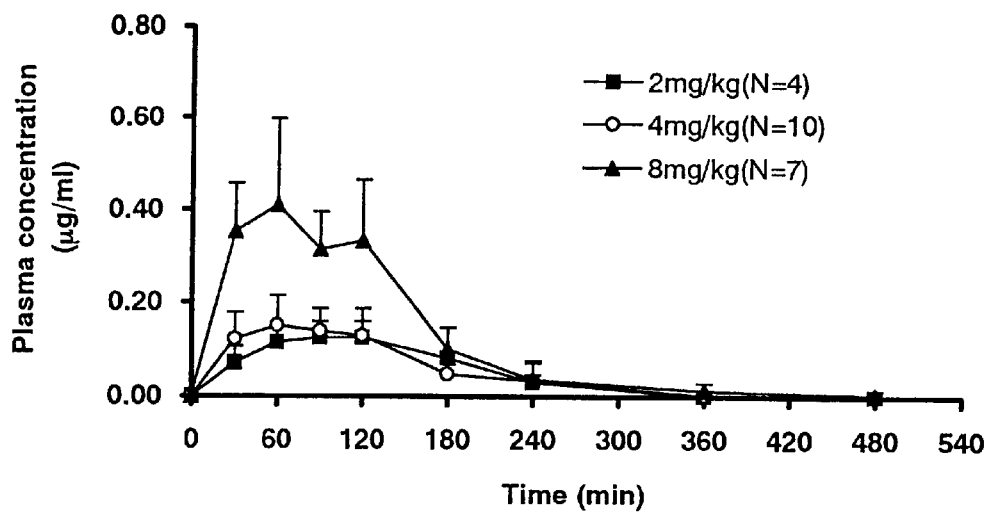
FIG. 4 shows a plasma concentration-time courses of the preparation of the present invention using an aqueous base at following doses. ■ indicates 2 mg/kg dose, ○ indicates 4 mg/kg dose and ▲ indicates 8 mg/kg dose.

Blood samples were collected from the jugular vein of the rats in a cage, at the time of 0, 0.5, 1, 2, 3, 4, 6, 8, and 10 hr. Plasma concentrations were measured by HPLC. The rayon cloths were recovered at 24 hr after the administration and the residual drug was extracted by 30 mL of methanol in a 50 mL centrifuge tube and measured its concentration by HPLC. The percent of apparent absorption was calculated and the absolute bioavailability was calculated from the AUC of percutaneous administration divided by the AUC of intravenous administration. These data were listed in Table 5 and FIG. 4.

TABLE 5

| Dose (mg/kg) | Cmax (μg/ml) | Tmax (min) | AUC 0–360 min (μg/ml * min) | BA (%) | Percent of apparent absorption (%) |
|---|---|---|---|---|---|
| 2 | 0.14 ± 0.03 | 75 ± 30 | 22.48 ± 1.88 | 30.92 ± 2.59 | 63.9 |
| 4 | 0.17 ± 0.06 | 93 ± 61 | 24.50 ± 4.33 | 17.86 ± 6.40 | 52.8 |
| 8 | 0.45 ± 0.15 | 51 ± 15 | 60.13 ± 24.63 | 22.68 ± 9.47 | 60.0 |

Experiment 6

The day before experiment, a dialysis probe of 2 mm membrane length was inserted into frontal cortex of non-fasting rats (Jcl Wistar strain male rat 9–11 W).

On the day of experiment, abdominal region hair was removed using a hair clipper and shaver under 2% halothane anesthesia. The aqueous basic formulation containing 5.6 mg/mL of Compound (I-1) was administered at a volume of 0.125, 0.25 and 0.5 mL to the rayon cloths which area were 2.5, 5, and 10 $cm^2$, respectively (Dose: 2, 4 and 8 mg/kg). Then the rayon cloths were placed on the abdominal region by support tape and covered with gum tape. After the administration, acetylcholine concentration in dialysate was measured every 30 min.

Figure 5:
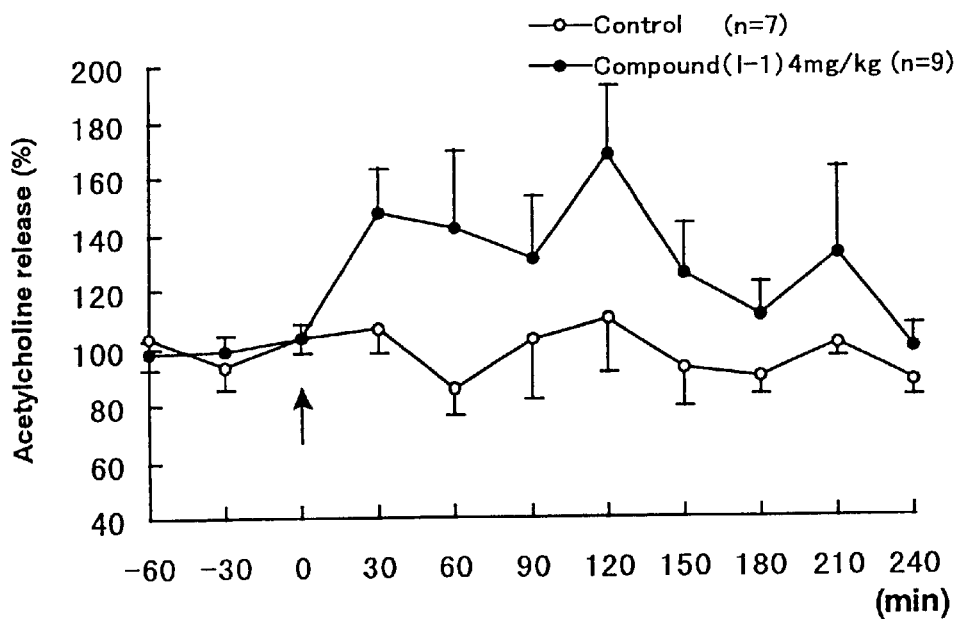
FIG. 5 shows a time-course of an acetylcholine release amount after administration of the preparation of the present invention. ○ indicates a control preparation containing only a base and ● indicates a preparation containing a base and Compound (I-1).
Figure 6:
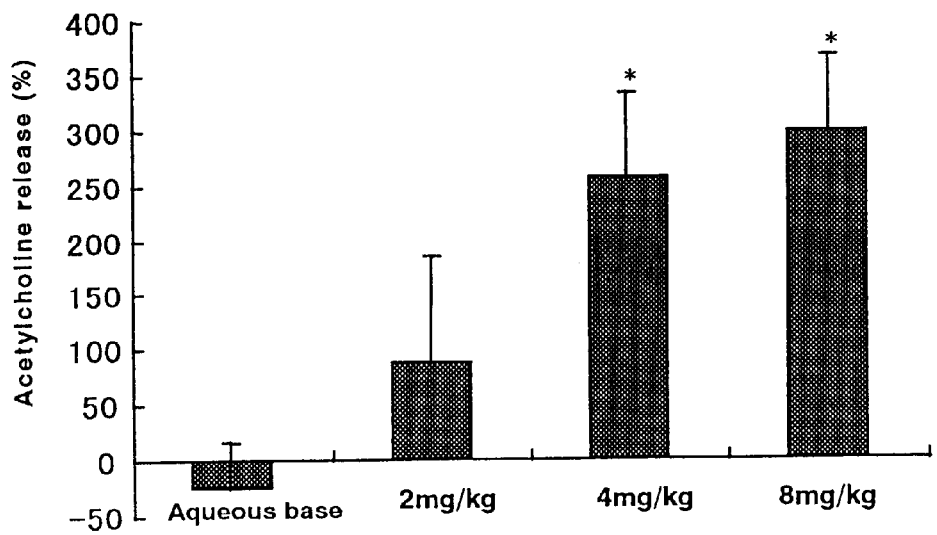
FIG. 6 shows an acetylcholine release amount after administration of the preparation of the present invention. Each bar indicates AUC value for 4 hrs after administration of a control preparation containing only a base and of preparations containing a base and Compound (I-1) (2 mg/kg, 4 mg/kg and 8 mg/kg).

FIG. 5 indicates a time-course of acetylcholine release after the administration of Compound (I-1). The plot data express the percent of control and the control level was monitored before the administration of Compound (I-1) in the same rat. The AUC values were calculated for 4 hrs of acetylcholine release as the percent of control in FIG. 6. These results clearly demonstrate the prolonged pharmacological effect by the percutaneously administrable preparations of the present invention.

Example 1

Ointments

To 990 mg of an oily base (2.5% 1-menthol/20% ethanol/77.5% isopropyl myristate), 10 mg of Compound (I-1) was added. After exposing of ultrasonic waves for 10–15 minutes, the mixture was stirred with a Vortex mixture to prepare a suspension. To a uniform mixture of 8.5 equivalent of white vaseline and 0.5 equivalent of liquid paraffin, 1 equivalent of the suspension was added and the mixture was stirred to prepare ointments.

Example 2

Ointments

Ointments were prepared in a similar method to that of Example 1 except that polyoxyethylene sorbitol monooleate was used in place of liquid paraffin.

Example 3

Ointments

Using 990 mg of an aqueous base (3% menthol/30% ethanol/67% phosphate buffer) and 10 mg of Compound (I-1), a suspension was prepared in a similar method to Example 1. After 4 equivalents of PEG and 5 equivalents of EG 4000 were uniformly mixed with heating, 1 equivalent of the suspension was added thereto. The mixture was stirred with cooling to prepare ointments.

Example 4

Tapes

Using 990 mg of an oily base (2.3% 1-menthol/25% ethanol/72.7% isopropyl myristate) and 10 mg of Compound (I-1), a suspension was prepared in a similar method to Example 1. After 5 equivalents of rubber polymer, 5 equivalents of α-pinene and 0.5 equivalent of liquid paraffin were uniformly mixed, 2 equivalents of the suspension was added thereto. The mixture was uniformly mixed and spread on a plastic film to prepare tapes.

Example 5

Poultices

Using 990 mg of an aqueous base (3% 1-menthol/30% ethanol/67% phosphate buffer, pH 4) and 10 mg of Compound (I-1), a suspension was prepared in a similar method to Example 1. After 5 equivalents of glycerin, 1 equivalent of kaolin and 5 equivalents of aqueous solution of polyvinyl alcohol were uniformly mixed, 2 equivalents of the suspension was added thereto. The mixture was stirred and the obtained paste was spread on non-woven cloths, which were covered with polyester film to prepare poultices.

Example 6

Patchs

Patchs were prepared in a similar method to Example 5 except that titanium oxide was used in place of kaolin and cloths was used in place of non-woven cloths.

INDUSTRIAL APPLICABILITY

As explained in the above experiments, the preparation of the present invention can keep a stable concentration of long duration in plasma by continuous release of an active ingredient, and therefore, the preparation can show continuous pharmacological effect. The preparation of the present invention is very useful as a sustained-release preparation containing Compound (I) as an active ingredient.

What is claimed is:

1. A percutaneously administrable preparation which comprises 2-(3-isoxazolyl)-3,6,7,9-tetrahydroimidazo[4,5-d]pyrano[4,3-b]pyridine, pharmaceutically acceptable salt or hydrate thereof and an aqueous base wherein 1-menthol is 2 to 3% by weight, ethanol is 20 to 30% by weight, a phosphate buffer wherein pH is 3 to 5 is 60 to 80% by weight, each percentage being with respect to the total amount of the base.

2. The percutaneously administrable preparation as claimed in claim 1 wherein 2-(3-isoxazolyl)-3,6,7,9-tetrahydroimidazo[4,5-d]pyrano[4,3-b]pyridine, pharmaceutically acceptable salt or hydrate thereof is 2-(3-isoxazolyl)-3,6,7,9-tetrahydroimidazo[4,5-d]pyrano[4,3-b]pyridine phosphate or hydrate thereof.

* * * * *